(12) United States Patent
Karlinsey

(10) Patent No.: US 9,023,373 B2
(45) Date of Patent: *May 5, 2015

(54) FUNCTIONALIZED CALCIUM PHOSPHATE HYBRID SYSTEMS FOR THE REMINERALIZATION OF TEETH AND A METHOD FOR PRODUCING THE SAME

(75) Inventor: Robert L. Karlinsey, Indianapolis, IN (US)

(73) Assignee: Indiana Nanotech, Indianapolis, IN (US)

(*) Notice: Subject to any disclaimer, the term of this patent is extended or adjusted under 35 U.S.C. 154(b) by 200 days.

This patent is subject to a terminal disclaimer.

(21) Appl. No.: 12/465,330

(22) Filed: May 13, 2009

(65) Prior Publication Data

US 2010/0291164 A1 Nov. 18, 2010

Related U.S. Application Data

(63) Continuation-in-part of application No. 11/701,210, filed on Jan. 31, 2007, now abandoned.

(51) Int. Cl.
| | | |
|---|---|---|
| A61K 9/68 | (2006.01) | |
| A61Q 11/00 | (2006.01) | |
| A61K 8/02 | (2006.01) | |
| A61K 8/21 | (2006.01) | |
| A61K 8/55 | (2006.01) | |
| A23L 1/035 | (2006.01) | |
| A23L 1/304 | (2006.01) | |
| A61K 8/11 | (2006.01) | |
| A61K 8/24 | (2006.01) | |
| A61K 8/362 | (2006.01) | |
| A61K 8/46 | (2006.01) | |

(52) U.S. Cl.
CPC ........... *A61Q 11/00* (2013.01); *A23L 1/035* (2013.01); *A23L 1/304* (2013.01); *A61K 8/0216* (2013.01); *A61K 8/11* (2013.01); *A61K 8/24* (2013.01); *A61K 8/362* (2013.01); *A61K 8/463* (2013.01); *A61K 2800/92* (2013.01)

(58) Field of Classification Search
CPC ............ A61K 9/68; A61K 8/02; A61K 8/21; A61K 8/55; A61Q 11/00
USPC ........................................ 424/401, 57, 48, 52
See application file for complete search history.

(56) References Cited

U.S. PATENT DOCUMENTS

| | | |
|---|---|---|
| 3,190,568 A | 6/1965 | Freedman et al. |
| 3,876,160 A | 4/1975 | Bloch |
| 4,018,619 A | 4/1977 | Webster et al. |
| 4,677,140 A | 6/1987 | Shioitsu |
| 5,053,212 A | 10/1991 | Constantz et al. |
| 5,342,441 A | 8/1994 | Mandai et al. |
| 5,833,954 A | 11/1998 | Chow et al. |
| 6,053,970 A | 4/2000 | Ison et al. |
| 6,126,097 A | 10/2000 | Chen et al. |
| 6,334,583 B1 | 1/2002 | Li |
| 6,840,961 B2 | 1/2005 | Tofighi et al. |
| 2002/0037258 A1 | 3/2002 | Dodd et al. |
| 2003/0069638 A1 | 4/2003 | Barlow et al. |
| 2003/0120351 A1 | 6/2003 | Tofighi et al. |
| 2003/0124066 A1 | 7/2003 | Dixon, Jr. et al. |
| 2003/0199615 A1 | 10/2003 | Chaput et al. |
| 2004/0101494 A1 | 5/2004 | Scott et al. |
| 2004/0126335 A1 | 7/2004 | Faller et al. |
| 2005/0025721 A1 | 2/2005 | Holme et al. |
| 2005/0084461 A1 | 4/2005 | Winston et al. |
| 2005/0241535 A1 | 11/2005 | Bohner |
| 2006/0175443 A1 | 8/2006 | Bysouth |
| 2006/0270752 A1* | 11/2006 | Xu et al. ................ 523/116 |
| 2007/0059379 A1* | 3/2007 | Gerber .................. 424/602 |
| 2007/0149650 A1 | 6/2007 | Masuda |
| 2007/0178220 A1* | 8/2007 | Karlinsey ............... 427/2.1 |
| 2007/0183984 A1 | 8/2007 | Haas et al. |
| 2008/0187500 A1 | 8/2008 | Karlinsey |
| 2008/0221681 A1 | 9/2008 | Trieu et al. |
| 2009/0324516 A1 | 12/2009 | Muscle et al. |
| 2010/0291164 A1 | 11/2010 | Karlinsey |

FOREIGN PATENT DOCUMENTS

WO 2007068062 6/2007

OTHER PUBLICATIONS

Schemehorn, et al., "Comparison of Fluoride Uptake into Tooth Enamel from Two Fluoride Varnishes Containing Different Calcium Phosphate Sources", The Journal of Clinical Dentistry, vol. 22, No. 2, 2011, pp. 51-54, http://premusa.com/Downloadablefiles/JCD_22_2_Schemehorn_et-al.pdf; entire document.

Walsh, "Evidence that demands a verdict: latest developments in remineralization therapies", Australasian Dental Practice, 2009, pp. 49-59, http://geriatricdentistry.com/wp/wp-content/uploads/2011/08/L.-Walsh-remin.article.pdf; p. 50, col. 2, paragraph 2; p. 51, col. 2, paragraphs 2-3, col. 3, paragraph 1.

Dushkin, "Potential of Mechanochemical Technology in Organic Synthesis and Synthesis of New Materials", Institute of Solid State Chemistry and Mechanochemistry, Siberian Branch of the Russian Academy of Sciences, UI. (Russia) Chemistry for Sustainable Development, vol. 12, 2004, pp. 251-273, XP002728802, http://www.sibran.ru/upload/iblock/4a3/4a30bb11b1f14.

Kim, et al., "Bioactive Organic-Inorganic Composite Prepared by Mechanochemical Method", Key Engineering Materials, Trans Tech Publications Ltd., Stafa-Zurich, CH, vol. 218-220, No. Bioceramics-14, Jan. 1, 2002, pp. 295-298, XP009127712, ISSN: 1013-9826, p. 296.

* cited by examiner

Primary Examiner — Audrea Buckley

(57) ABSTRACT

A dental remineralizing system, including a functionalized calcium-containing complex having an organic surfactant component mechanochemically attached to a distressed calcium phosphate component and blended with the comestible material.

19 Claims, 15 Drawing Sheets

Ca++ dissolution profiles for β-TCP, mTCP, and TCP-SLS. Curves were generated (as indicated by solid lines) by modeling the data to an extended Langmuir equation.

Ca++ dissolution profiles for b-TCP, mTCP, and TCP-FA Curves were generated (as indicated by solid lines) by modeling the data to an extended Langmuir equation.

Mean ± SEM data are shown for (a) the change in Vickers microhardness from baseline ($\Delta VHN = VHN_{post} - VHN_{base}$) and (b) fluoride uptake into enamel specimens (N=3) after six days of pH cycling for Groups 1: distilled water; 2: 500 ppm F; 3: 500 ppm F + 100 ppm fTCP

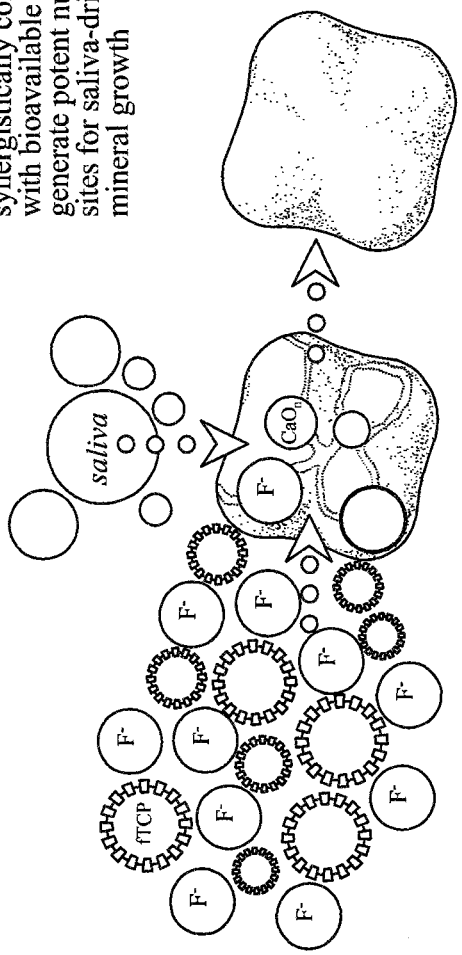

FUNCTIONALIZED CALCIUM PHOSPHATE HYBRID SYSTEMS FOR THE REMINERALIZATION OF TEETH AND A METHOD FOR PRODUCING THE SAME

CROSS-REFERENCE TO RELATED APPLICATIONS

This application is a continuation-in-part of and claims priority to co-pending utility patent application Ser. No. 11/701,210 filed Jan. 31, 2007 now abandoned and published as U.S. Patent Pub. No. 2007/0178220.

TECHNICAL FIELD

The present novel technology relates generally to chemistry and, more particularly, to functionalized calcium-releasing hybrid moieties and their dental remineralization applications.

BACKGROUND

The tooth is an interesting structure having layers of soft inner media covered by a hard outer surface. A pulp chamber maintains the blood and nerve supply and is protected by the hard dentin layer, which attenuates shock and pressure experienced during mastication or in the event of a traumatic event. An outer layer of enamel covers the dentin. The inorganic mineral content in dentin is quite low compared to enamel, with the calcium weight fractions in dentin about 28% lower than in enamel. The decreased mineral content in dentin is compensated for by an equivalently elevated weight fraction of organic constituents. Although the Ca:P ratios in both calcium and dentin are about the same, the specific surface areas differ markedly: 77 $m^2/g$ for enamel and 94 $m^2/g$ for dentin. One reason for the increased surface area of dentin may be attributed to collagen tubules manifested within the dentin matrix, which help provide structure and support.

Tooth enamel is comprised of a heterogeneous arrangement of inorganic mineral and less than 1% organic substances, including proteins and collagen. The overall thickness of human enamel can be up to several millimeters and visually, the apatite crystals bear a hexagonal arrangement, although the actual unit cell pertaining to hydroxyapatite is likely comprised of two different sets of monoclinic crystal arrangements, with one monoclinic arrangement arising from two hexagonal cells. Typical enamel crystallites have dimensions of about 40 nm wide and at least 300 nm long, with adjacent prisms separated interproximally by a substance comprised of organic and inorganic matter that is somewhat more resistant to caries formation. The apatite crystals found in enamel predominantly manifest hydroxyl or carbonate species. Additionally, these crystals may also have magnesium, strontium, and sodium substituted for calcium.

Dissolution of the enamel prisms occurs during an acid attack leading to demineralization. The nature of the acid challenge is distinguished between cariogenic and erosion; for the latter, acid reflux or consumption of acid beverages, for example, leach mineral from the crystal, creating macroscopically smooth and rounded characteristics of the enamel, while the microstructure reveals significant pitting and jaggedness. With respect to the cariogenic type of enamel weakening, acid-producing bacteria, such as *Streptococcus mutans*, adhere to the tooth and ferment carbohydrates containing sucrose consumed during eating events. This activity produces lactic acid which then eats away at the enamel structure to create subsurface lesions that may ultimately progress to cavitations, or dental caries. Microscopically, the demineralization process occurs primarily at the center surface of the enamel prism and propagates downwards through the body of the prism, ultimately proceeding outwards to the prism walls. The prism surface manifests species such as $OH^-$ and $CO_3^{2-}$ residing at the center of the crystal. Although this occupancy helps to stabilize the apatite structure, these species are highly prone to dissolution relative to $Ca^{2+}$ and $PO_4^{3-}$, which reside on the corners and faces of the crystal arrangement.

The thermodynamic progressions of remineralization to apatite, coupled with the relatively low levels of inorganic mineral constituents naturally found in saliva, are often unable to keep pace with the rate of demineralization. Even further problematic, for instance, salivary flow is often reduced for individuals taking medications, including aspirin or antihistamines. It follows then the already low calcium salivary levels will likely be affected resulting in an increased risk for enamel demineralization.

Other means, such as fluoride, could be utilized to help restore enamel strength more proactively. Fluoride has a rich and clinically-proven history of preventing dental decay. First added to drinking water in low levels, topical fluorides have evolved into such common vehicles as toothpaste and mouth rinses. These relatively inexpensive forms of topical dental therapy are quite appealing and will likely become even more so as the views of patients and practitioners shift even further to prevention instead of restoration, the latter of which is typically considered to be more costly and painful.

Even through fluoride applications and other preventive measures, dental decay still affects the majority of the world's population. A US study conducted by the National Health and Nutrition Examination Survey recently reported that while dental decay has not increased in the last 25 years for most of the US population, dental decay is on the rise in children between 2 and 11 years old. This apparent epidemic suggests that fluoride alone, despite its great clinical success and acceptance, may be insufficient.

Further, while many drinks and other comestibles are currently fortified with calcium, the calcium is typically added in the form of a highly soluble precursor, such as calcium gluconate, calcium lactate or the like. While such highly soluble calcium is advantageous for quick and efficient absorption through the stomach and intestines, such rapid dissolution is less desirable for a calcium supplement intended to reside in the mouth for sufficient time to promote remineralization of the teeth. For such remineralization a relatively slow and steady calcium supply is more desirable. Tricalcium phosphate is a cheap, plentiful and rich calcium source with a very slow calcium release rate. Unfortunately, conventional calcium phosphate materials dissolve too slowly and such technologies are only marginally effective in providing useful quantities of minerals to the teeth.

Thus, there remains a need for mineral delivery compounds that reside in the mouth and that directly boost remineralization efficacy via direct application to the tooth. The present novel technology addresses this need.

SUMMARY

The present novel technology relates generally to the solid-state generation of functionalized calcium-releasing hybrid moieties as well as to their inclusion in mints, candies, gums, lozenges, and other comestible, confectionery and foodstuff formats in order boost remineralization efficacy of the dentition, as well as to provide cosmetically-important whitening of the enamel.

One object of the present novel technology is to provide an improved method of producing functionalized calcium phosphate hybrids. Another object of the present novel technology is to provide an improved dental delivery system incorporating functionalized calcium-releasing hybrid moieties for the purposes of delivering useful minerals to teeth. Further objects, features, and advantages will become apparent from a consideration of the following description.

BRIEF DESCRIPTION OF THE DRAWINGS

FIG. 9 schematically illustrates dental remineralization according to one embodiment of the present novel technology.

DETAILED DESCRIPTION

Figure 1:
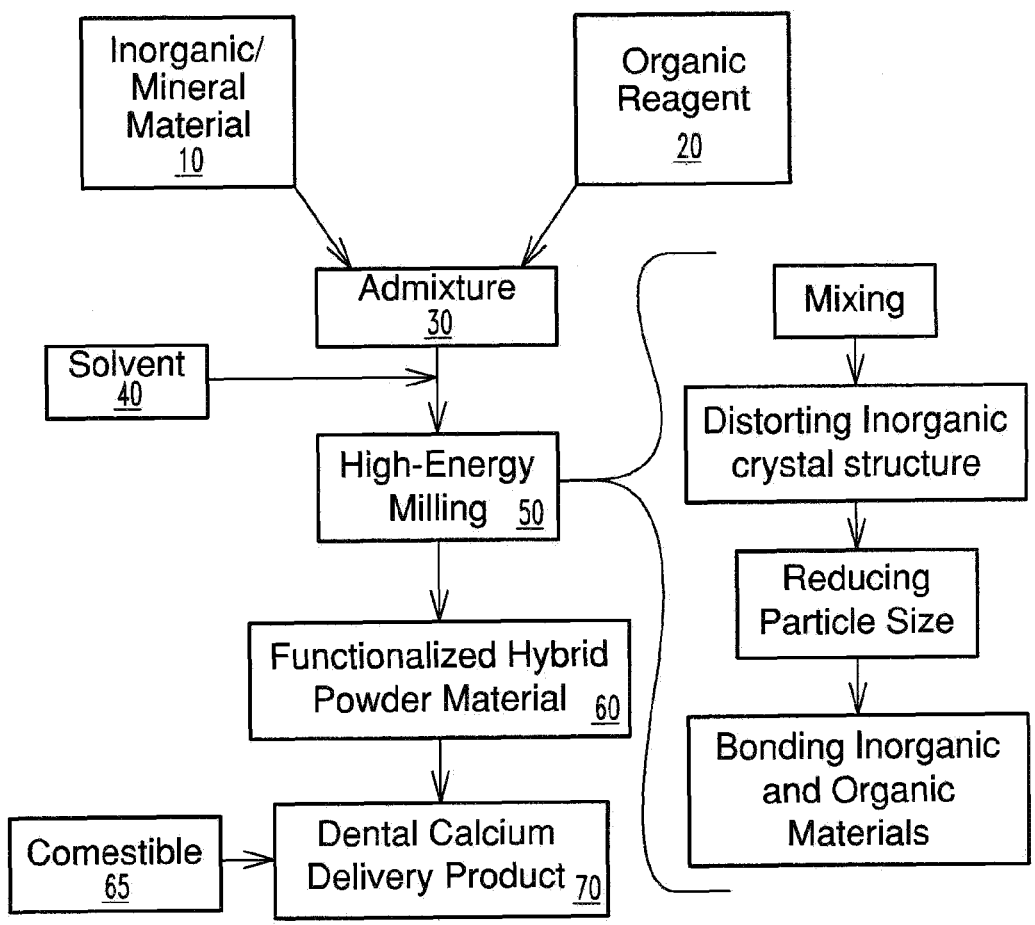
FIG. 1 is a flow chart representing a process for producing functionalized moieties according to the present novel technology.

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

The present novel technology relates to calcium-releasing functionalized hybrid moieties capable of releasing relatively large quantities of calcium and/or other predetermined minerals at a predetermined rate sufficient to assist in the remineralization of teeth, as well as the production of such functionalized moieties and their uses in dental delivery system. The present novel technology also relates to a solid-state, mechanochemical method for producing a thermodynamically and kinetically stable material that releases ions and moieties, such as calcium, at a predetermined and controllable rate due to the complex chemistry created during the solid-state alloying process. As the present novel solid-state alloying technique was developed in part to address a need for, among other things, improved dental pastes, gels, dentifrices, varnishes, mints, gums, lozenges, and other confectionery and foodstuff formats, the following examples and embodiments tend to reflect and relate to chemistries having dental remineraiization applications. However, it should be kept in mind that the present novel technology is broadly applicable beyond the specific dental applications discussed herein.

One aspect of the present novel technology relates to the application of calcium-releasing functionalized hybrid materials that may provide improved dental benefits to consumers by delivering high surface area-to-volume ratio, organically functionalized mineral particles to a substrate, such as dentition. The functionalized surface aids in promoting direct contact between a target material (such as the pellicle, enamel, or the like), and therefore allows for more efficient delivery of a desired mineral component (such as calcium and phosphate).

In one specific aspect of the present novel technology, the novel chemical synthesis method as detailed hereinbelow exploits a high-energy mechanochemical ball milling process to produce a relatively large amount of functionalized complexes with high efficiency. Typically, the functionalized complexes are blends of independent organic and inorganic reagents mechanochemically coupled together to yield a hybrid material with predetermined physical and chemical properties. A typical inorganic reagent may include a calcium phosphate mineral, such as calcium phosphate tribasic, calcium phosphate dibasic, dicalcium phosphate, or the like. Alternatively, other inorganic materials may include sodium, magnesium, iron, silicon, aluminum, manganese, titanium and the like in various mineralogical forms (such as oxides, phosphates, carbonates, nitrides and the like).

Typical organic materials include anionic surfactants (such as sodium lauryl sulfate, sodium lauryl ether sulfate, ammonium lauryl sulfate, N,N-Dimethyl-N-[3-(sulfoxy)propyl]-1-nonanaminium hydroxide inner salt, sodium dodecylbenzenesulfonate, poly(ethylene glycol) 4-nonylphenyl 3-sulfopropyl ether potassium salt, doctyl sulfosuccinate sodium salt, and the like), cationic surfactants (such as pyridinium chloride, hexadecyltrimethylammonium bromide, N,N-cimethyl-N-[3-(sulfoxy)propyl]-1-decanaminium hydroxide inner salt, and the like), neutral surfactants-polyethers or polyesters (such as polyethylene glycol, polypropylene glycol (PPG), poly(ethylene glycol)-block-poly(propylene glycol)-block-poly(ethylene glycol), poly(ethylene oxide)-block-polycaprolactone, polycaprolactone diol, polycaprolactone triol, and the like), carboxylic acids (such as fumaric acid, acrylic acid, malic acid, citric acid, maleic acid, stearic acid, and the like), polymethyl methacrylate, or the like. Other commonly selected organic reagents may include those materials with properties akin to those species listed above.

Mechanochemical Ball Milling

While ball milling is typically employed with the goals of reducing particle size and significantly distorting morphological order, the present novel technology uses ball milling primarily as a method of mechanochemically blending the individual components while maintaining the morphological and/or property integrity of at least the major substantial component in the material blend. In turn, this allows for tailored and/or improved properties and characteristics of the blended material when used as a component of various formulations. The size-reduction and lattice distortion effects of high-energy ball milling are thus used to distort the lattice structure of particles of the inorganic precursor material such that they can be physically fused, bonded and/or otherwise connected to the organic precursor material to build, rather than tear down, organically functionalized hybrid moieties.

Mechanochemical (MC) ball milling impacts disparate materials together with sufficient force to form new hybrid or composite materials. These MC milling and hybrid formation processes occur entirely in the solid state, distinguishing MC ball milling from traditional milling. This quasi-destructive process deforms components through powerful collisions between ball-particle, particle-wall, and particle-particle, creating significant grain boundaries at the nanoscale where components have fractured and fused. One convenient milling apparatus for accomplishing MC hybrid generation is the planetary ball mill. The planetary ball mill lends itself to the MC process since in order to generate the energy required for such concurrent fracturing and fusion, the vessel containing the balls and material is typically rotated at high speed opposite to the direction of rotation of the platform on which the vessel is placed. These concurrent physical and chemical processes enable the synthesis of hybrid materials having properties and characteristics atypical of materials prepared by the usual synthetic procedures and thus contribute to a myriad of new opportunities. The MC process may likewise be carried out in traditional rotor mills, so long as sufficient kinetic energy of the milling media may be achieved to fracture and fuse the inorganic and organic precursors.

The current novel technology introduces efficiencies of cost, time, and scale of producing blended materials characterized by specific, predetermined properties without the need for sophisticated chemistries and/or multiple specialized apparatti. The resulting scaleability may then be realized for applications where localized chemical, mineral or drug delivery is desired.

The novel technology exploits the mechanochemical ball milling process to produce a relatively great amount of relatively inexpensive hybrid materials in a relatively short time. Typically, the hybrid materials are blends of independent organic and inorganic reagents coupled together to yield a blended material characterized by properties similar to those of the starting materials. Typical inorganic materials include minerals (calcium, magnesium, and the like, in oxide form, carbonate form, or the like), clays, rare-earth and metal oxides, or the like, and/or typical organic materials including hydrophilic and hydrophobic molecules, or the like. For example, hybrid silica-carbamide-calcium phosphate systems may be produced in various formulations for improving anti-erosion, remineralization and/or anti-sensitivity efficacy of an oral rinse or paste.

Hybrid Synthesis and Characterization

The preparation of organic-inorganic materials via a mechanochemical process is illustrated in FIG. 1 and described as follows. Depending upon the desired composition, the mixture may range from between about 0.5 and 99.5 weight percent inorganic precursor material, with the balance being organic precursor material.

Typically for the synthesis of organically functionalized TCP, the inorganic starting material 10 is beta tricalcium phosphate ($\beta$-TCP) and the organic starting material 20 is an organic surfactant (such as sodium lauryl sulfate or SLS), an edible acid (such as fumaric acid or FA), a polymer (such as polyvinyl chloride or PVC); however, any convenient inorganic and organic surfactant precursors 10, 20 may be selected to yield a resultant hybrid material having the desired properties. Tricalcium phosphate (TCP, $Ca_3(PO_4)_2$) 10 plus an organic precursor 20 are combined to define an admixture 30. The admixture 30 is typically added to a vessel containing a plurality of milling media balls, such as ten 20-millimeter diameter balls. The admixture 30 typically contains between about 0.1 and 30 weight percent organic precursor 20 with the balance substantially TCP 10, more typically contains between about 1 and about 10 weight percent organic precursor 20, and still more typically between about 2 and about 5 weight percent organic precursor 20. Additionally, a small amount of an organic solvent 40, such as pentane, is typically added as a lubricant. Once loaded with the admixture 30 and milling media, the vessel is typically operationally connected to a mill, such as locked onto the sun wheel of a planetary ball mill. The vessel is then agitated, such as rotated unidirectionally and opposite the rotational direction of the sun wheel in the case of a planetary mill, at a sufficiently high speed and for a sufficient duration of time (high-energy milling 50) to yield functionalized chemical moieties, such as, for example, at least about 400 rpm for about two hours. At the end of the milling process 50 the resulting hybrid powder 60 is substantially composed of functionalized moieties.

The resultant powder 60 is then filtered from the balls and stored, such as in plastic containers. The powder may also be sized, such as through a sieving process, prior to storage. Typically, useful particle size for functionalized moieties is in the range from about 0.1 microns to 20 microns, although specific uses and applications may demand particles of greater or lesser dimension.

After the functionalized moieties 60 are recovered in powder form, they may be added to dental hygiene materials or comestibles 65 to yield improved dental repair products 70. The solubility of a respective functionalized moiety powder 60 made as described above is a function of the amount of organic precursor 20 used and the attachment of the organic precursor 20 to the calcium phosphate 10. Such dental products 70 may include pastes, gels, varnishes and the like and such comestibles 65 may include candies, mints, gums, lozenges and the like. It should be noted that the short-range order of the functionalized hybrid material 60 is substantially preserved in the $\beta$-TCP structure, despite the aggressive nature of the mechanochemical milling process.

Milling Studies

Figure 2A:
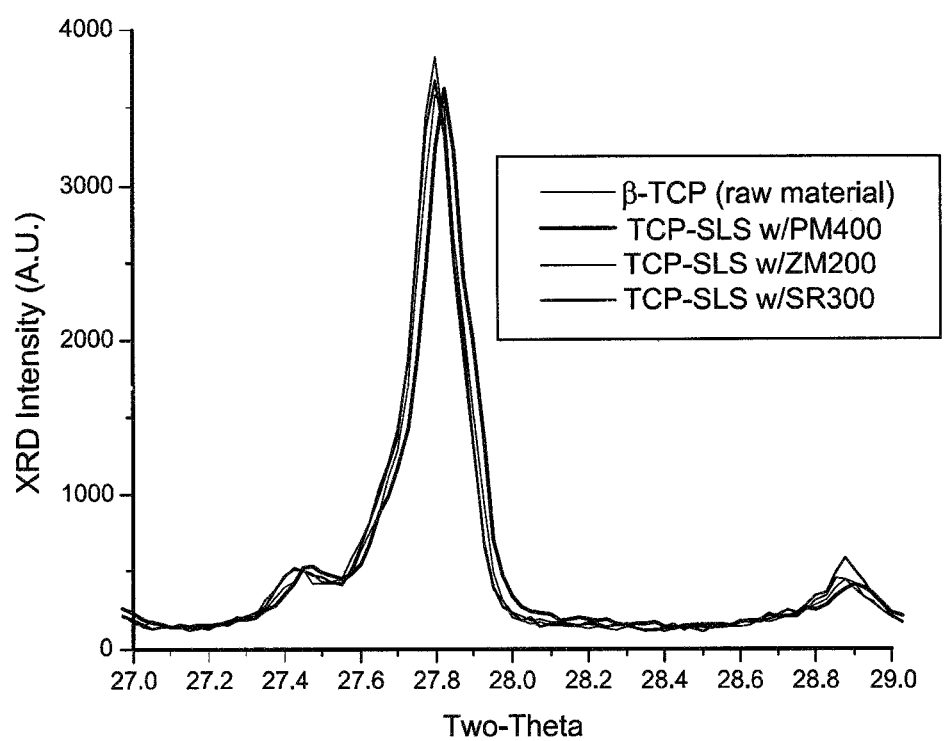
FIG. 2A is a first XRD plot showing the lattice distortion of β-TCP as milled by various techniques according to the present novel technology.
Figure 2B:
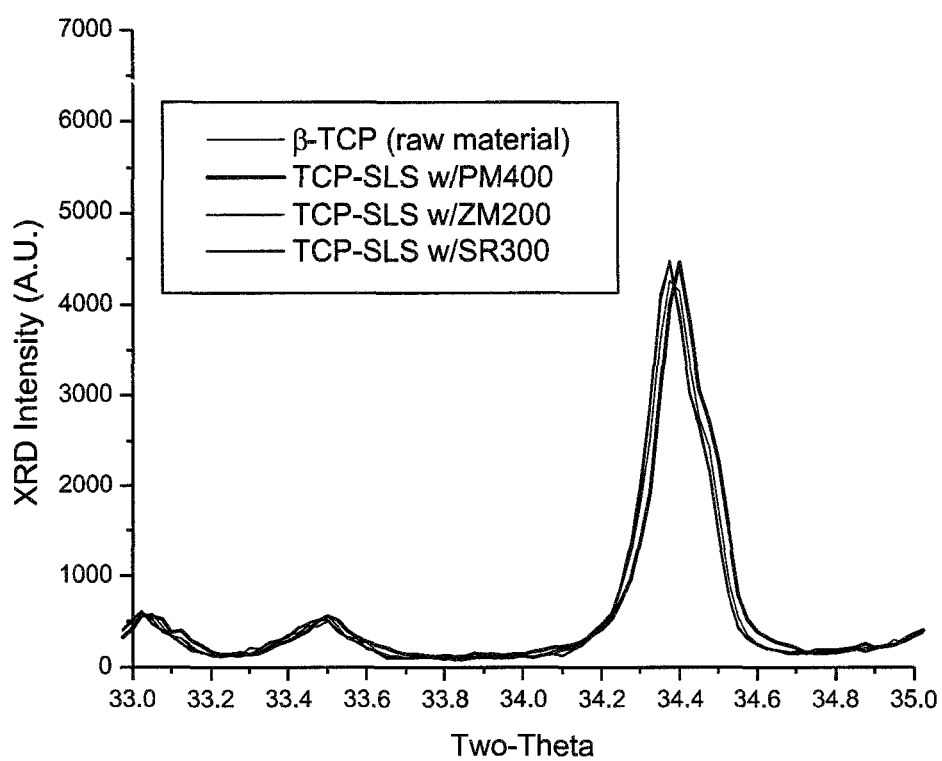
FIG. 2B is a second XRD plot showing the lattice distortion of β-TCP as milled by various techniques according to the present novel technology.
Figure 2C:
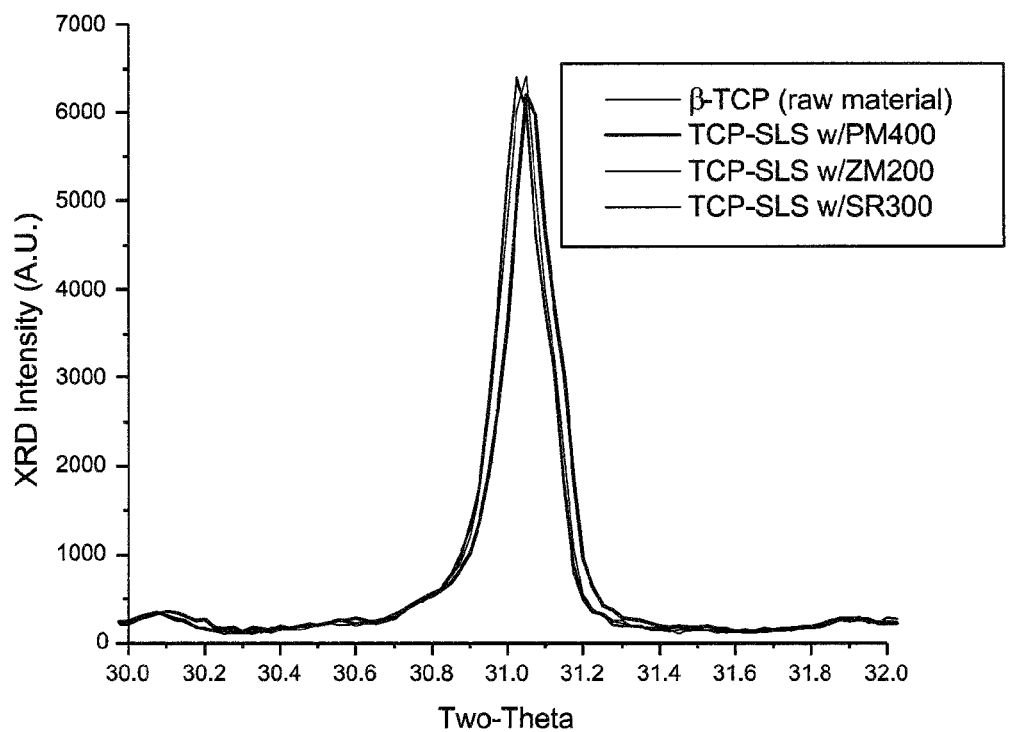
FIG. 2C is a third XRD plot showing the lattice distortion of β-TCP as milled by various techniques according to the present novel technology.
Figure 3A:
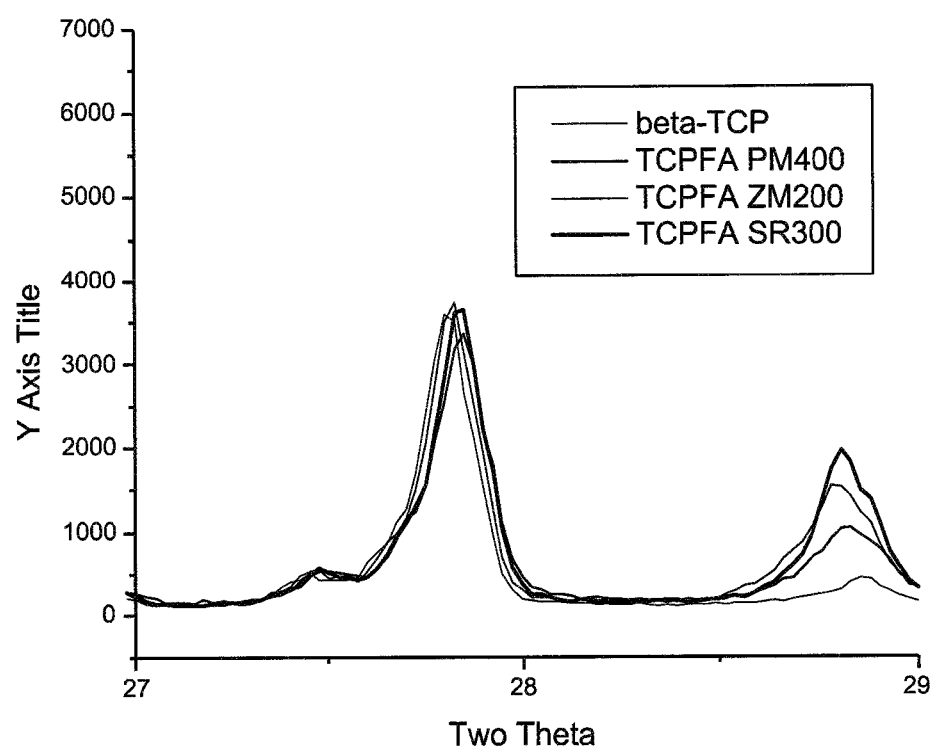
FIG. 3A is a fourth XRD plot showing the lattice distortion of β-TCP as milled by various techniques according to the present novel technology.
Figure 3B:
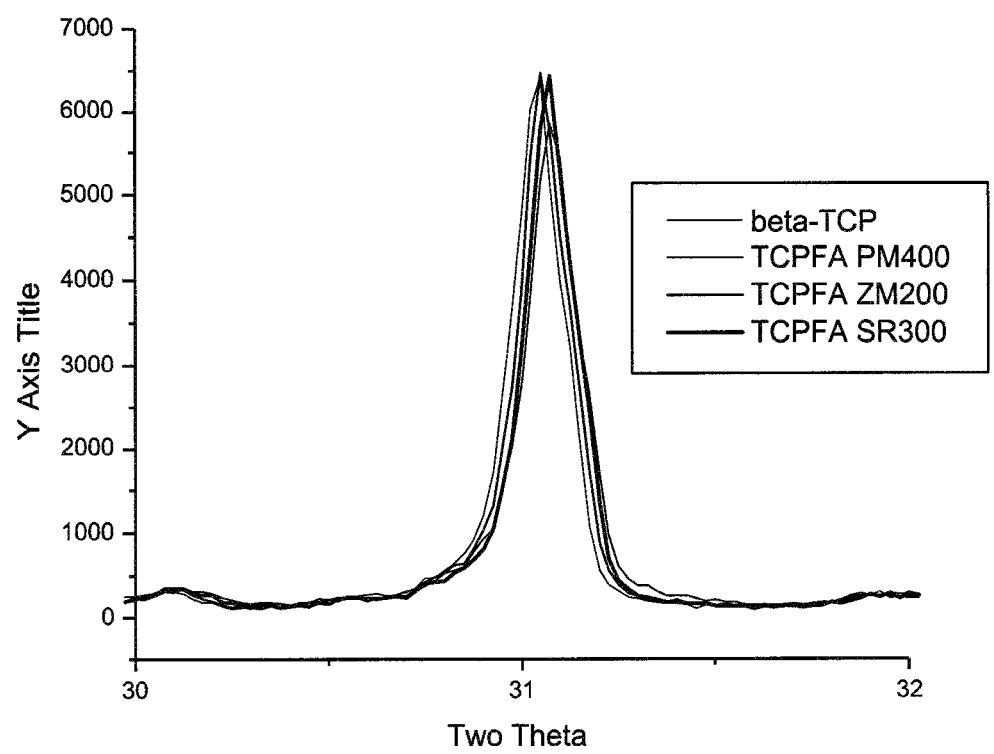
FIG. 3B is a fifth XRD plot showing the lattice distortion of β-TCP as milled by various techniques according to the present novel technology.
Figure 3C:
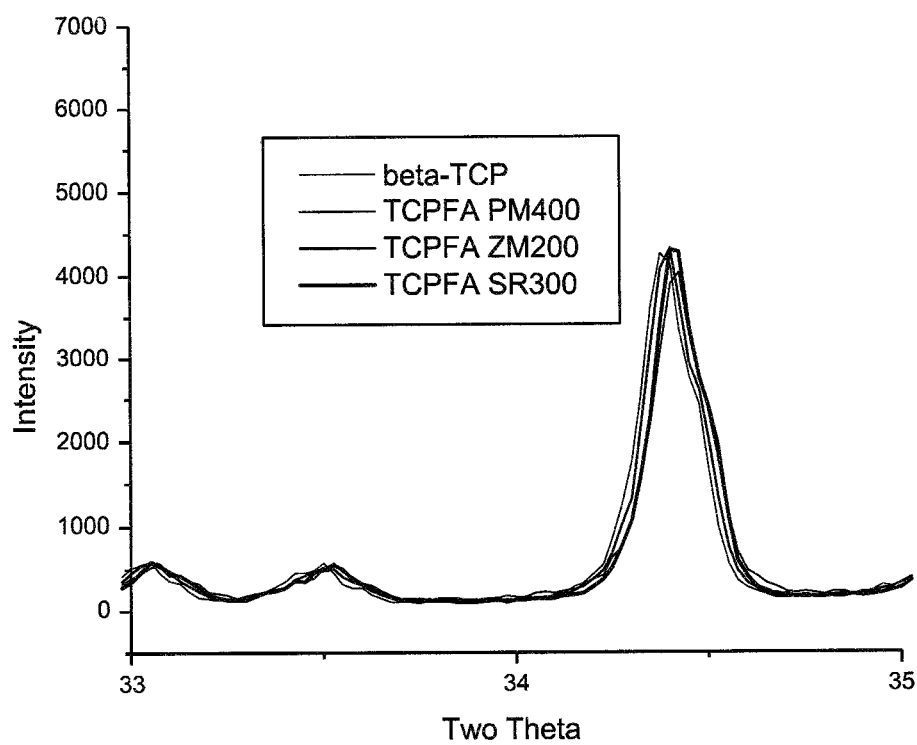
FIG. 3C is a sixth XRD plot showing the lattice distortion of β-TCP as milled by various techniques according to the present novel technology.

FA and SLS functionalized TCP samples were prepared using three different mills to investigate the effects of milling variations on the resultant hybrid materials 60. A planetary mill (PM400) and two rotor mills (SR300 and ZM200), all from Retsch Inc., 74 Walker Lane, Newtown, Pa., 18940, were used. For the SLS-TCP samples, an admixture 30 of 2 weight percent SLS with the remainder being β-TCP was prepared in a vessel for milling as described above; for the FA-TCP samples, an admixture of 10 weight percent FA with the remainder being β-TCP was prepared in a vessel for milling as described above. Identical weights of samples were milled for 2 hours at 375 RPM on the PM400, for 2 minutes at 8000 RPM on the SR300, and 2 minutes at 16000 RPM on the ZM200. XRD analyses of the resultant milled hybrid materials 60, along with a β-TCP were test standard, were obtained and are reproduced as FIGS. 2A-2C.

For the SLS-TCP samples, slight shifting of the characteristic β-TCP peaks (about 0.02 degrees) were observed for the PM400 milled specimen; however, this shifting was within detector resolution and was reproducible. No significant β-TCP peak shifting was observed for the SR300 or ZM200 milled samples. For the FA-TCP samples, shifting of the characteristic β-TCP peaks of between about 0.025 and 0.05 degrees was observed for the PM400 and SR300 milled specimens, with dubious shifting of the ZM200 peaks likewise observed. Thus, it appears that the type of mill is less important than the combination of milling time and speed; there appears to be a minimum time/speed, or milling energy, threshold below which significant lattice distortions are not generated. Since the presence of lattice distortions likely offers opportunity for the organic component 20 to bind with the distorted inorganic component, whether through a physical mechanism, a chemical mechanism, or some combination of both, milling at times/speeds or energies above the lattice distortion threshold is likely most advantageous for the generation of hybrid moieties 60.

Figure 4A:
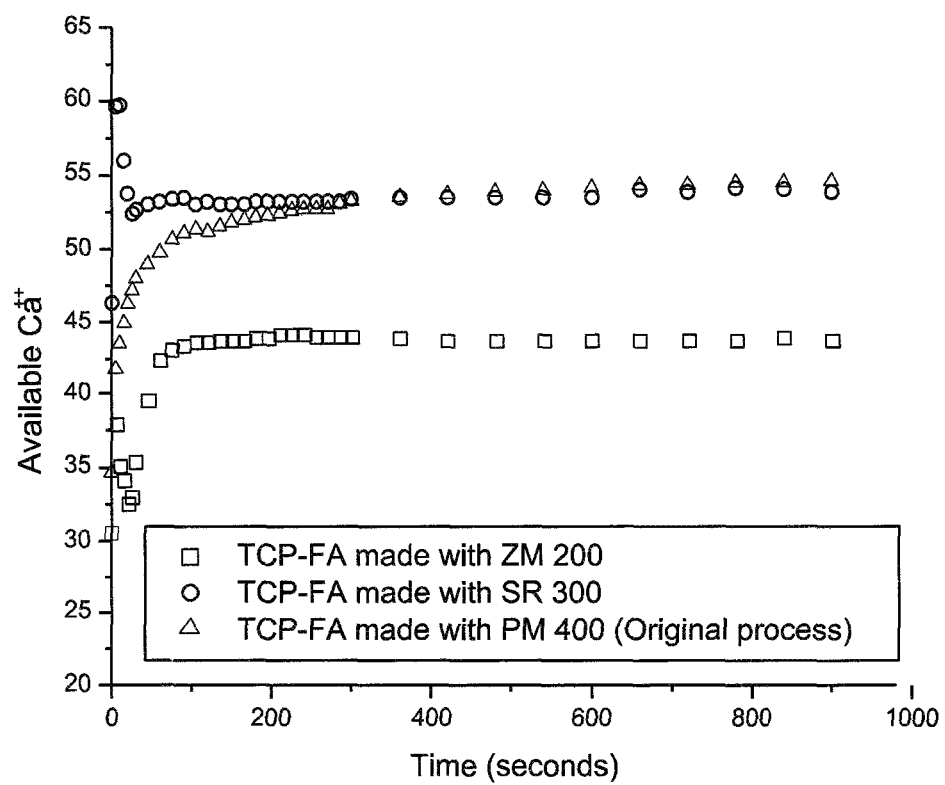
FIG. 4A is a first plot of calcium bioavailability of FA-TCP as milled by various techniques according to the present novel technology.
Figure 4B:
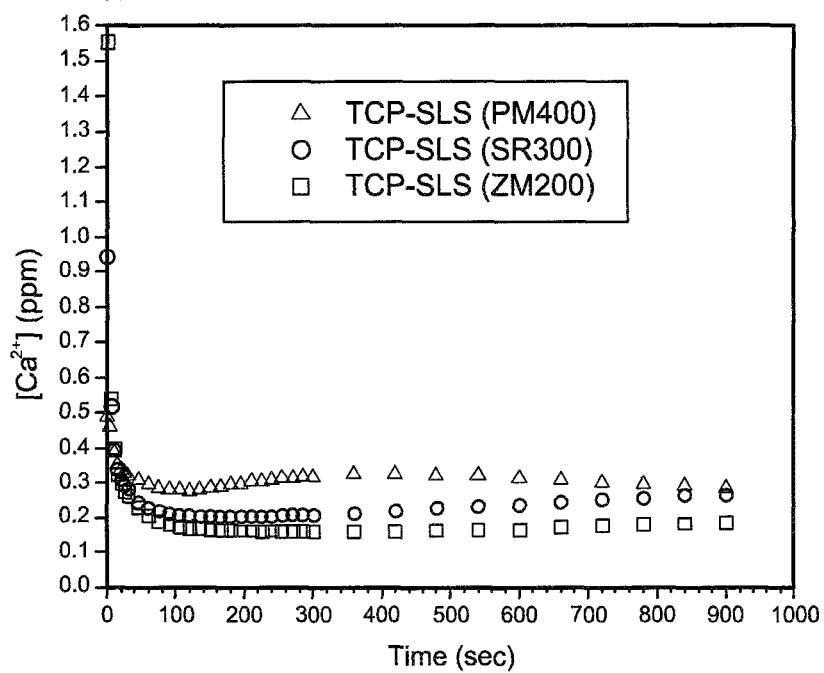
FIG. 4B is a first plot of calcium bioavailability of SLS-TCP as milled by various techniques according to the present novel technology.

The calcium release rates for the above-describes samples were measured, and reproduced as FIGS. 4A and 4B. The calcium bioavailability is substantially greater for the PM400 and SR300 milled FA-TCP samples than for the ZM200 milled sample. Likewise, the calcium bioavailability of the PM400 milled SLS TCP sample is substantially greater than those of the SR300 and ZM200 milled samples. This agrees with the above lattice distortion data, insofar as the most distorted samples, relative to β-TCP, also exhibit the greatest calcium bioavailability. While the presence of organic functionality on the hybrids 60 allows for the tailorability of certain properties, the lattice-distorting effects of high-energy milling on β-TCP alone is sufficient to increase its calcium dissolution rate and thus its calcium bioavailability.

TABLE 1

Figure 5A:
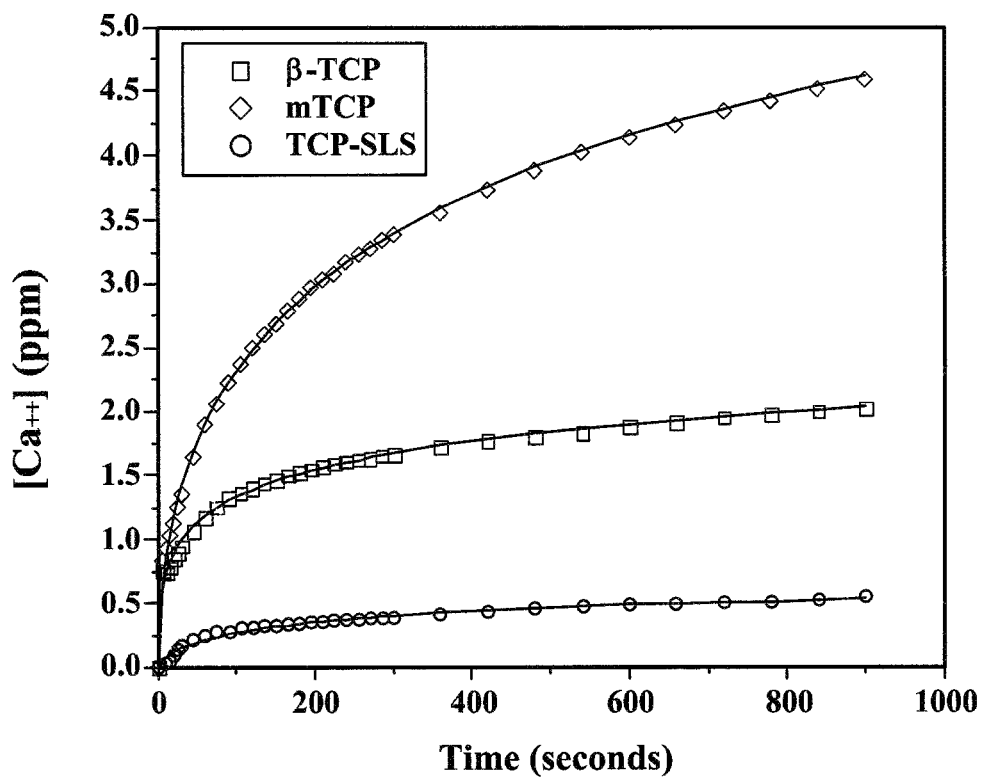
FIG. 5A is a first plot of the dissolution profiles for β-TCP, milled TCP and SLS-TCP according to a first embodiment of the present invention.

Listing of common calcium phosphate salts and minerals used for potential tissue strengthening or remineralization applications.
Common Calcium Phosphate Salts & Minerals Calcium chloride, $CaCl_2$
Calcium lactate, $CaC_6H_{10}O_6$
Calcium glycerophosphate, CaGP, $CaPC_3H_9O_6$
Amorphous calcium phosphate, ACP, formula varies
Tetracalcium phosphate, TTCP, $Ca_4O(PO_4)_2$
α-tricalcium phosphate, α-TCP, $Ca_3(PO_4)_2$
Dicalcium phosphate dihydrate, DCPD, $CaHPO_4 \cdot 2H_2O$
Octacalcium phosphate, OCP, $Ca_8H_2(PO_4)_6 \cdot 5H_2O$
β-tricalcium phosphate, β-TCP, $Ca_3(PO_4)_2$
Hydroxyapatite, HAP, $Ca_{10}(PO_4)_6(OH)_2$ Dissolution Studies The aqueous solubility was of SLS-TCP and FA-TCP samples prepared as described above were measured and compared to the solubility of unmilled β-TCP reference material as well as to milled and distorted but nonfunctionalized TCP. FIG. 5A illustrates the relative solubility of SLS functionalized TCP 60 as compared to that of β-TCP and milled TCP. The milled TCP and the β-TCP start out with similar dissolution, but the milled TCP dissolves more quickly than the β-TCP. In contrast, the dissolution profile of the SLS-TCPO 60 sample begins and remains over time substantially lower than that of either of the non-functionalized samples.

Figure 5B:
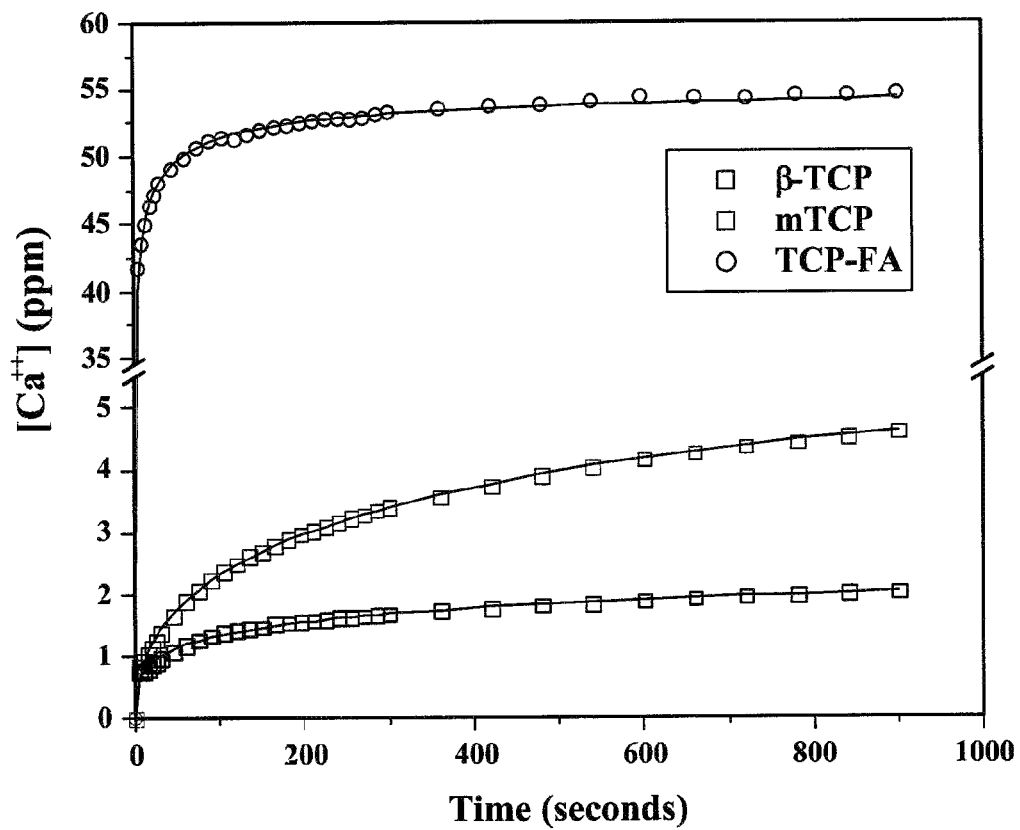
FIG. 5B is a first plot of the dissolution profiles for β-TCP, milled TCP and FA-TCP according to a first embodiment of the present invention.

Conversely, as shown in FIG. 5B, the FA-TCP starts out with a dissolution profile over an order of magnitude greater than those of the non-functionalized samples and remains so over time. Thus, while the milling process alone increase the dissolution profile of β-TCP by a factor of about 3, functionalizing β-TCP with SLS decreases its dissolution profile by about a factor of 5 to 10 while functionalizing TCP with FA increases its dissolution profile by a factor of about 10 to 20. Clearly, by properly selection the organic functional group physical parameters such as solubility may be dramatically increased or decreased as desired.

In Vitro Enamel Remineralization Using Functionalized TCP and Fluoride

Fluoride and calcium are both important tools for the remineralization of teeth, but are not introduced together as the presence of calcium can compromise fluoride bioavailability. Fluoride is very reactive with calcium and rapidly forms calcium fluoride in an aqueous environment, such as the oral cavity. However, organic functionalization of an inorganic calcium source, such as β-TCP, can impede the formation of calcium fluoride and thus render both the calcium and fluoride bioavailable for dental remineralization.

SLS-TCP 60 was prepared as described above (milled in a PM400 planetary ball mill) and having a 2 weight percent SLS-98 weight percent TCP composition.

Preparation and execution of in vitro performance testing on bovine enamel were performed as follows. 3 mm enamel cores were drilled from clean bovine incisors and mounted in acrylic rods. The cores were then ground and polished, and then cleaned through sonication and rinsing. The specimens were immersed in vials containing carbopol-lactic acid solution partially saturated with hydroxyapatite and adjusted to a pH of 5.0. These vials were subsequently loaded into an incubator at 37° C. to establish 'white-spot' (non-cavitated) lesions. The white spot lesions were characterized by a dense surface mineral zone approximately 15 microns thick (via polarized light microscopy), while lesion depth extends to about 70 μm (via microradiographic analysis and reflective microscopy). After immersion for 36 hours, specimens were removed from the solution, rinsed, and measured for baseline Vickers microhardness. Specimens exhibiting mean Vickers hardness numbers (VHN) between 25 and 45 were selected for the study and stratified into the eight groups (N=9) having an overall mean VHN of about 33 VHN (for reference, sound bovine enamel typically has a VHN between 300 and 350).

The in vitro pH cycling model used to investigate the effects of fluoride with functionalized TCP 60 is summarized in Table 2.

TABLE 2

Outline of daily remineralization and demineralization events and duration employed in the dental model evaluating reversal of white-spot enamel lesions.

| Event | Duration |
|---|---|
| Treatment #1* | 2 minutes |
| Artificial Saliva, pH = 7.0 | 1 hour |
| Treatment #2 | 2 minutes |
| Artificial Saliva, pH = 7.0 | 1 hour |

TABLE 2-continued

Outline of daily remineralization and demineralization events and duration employed in the dental model evaluating reversal of white-spot enamel lesions.

| Event | Duration |
|---|---|
| Acid Challenge, pH = 5.0 | 4 hours |
| Artificial Saliva,** pH = 7.0 | 1 hour |
| Treatment #3 | 2 minutes |
| Artificial Saliva, pH = 7.0 | 1 hour |
| Treatment #4 | 2 minutes |
| Artificial Saliva, pH = 7.0 | Overnight |

*On Day one, specimens were pre-conditioned for one hour in artificial saliva prior to the first treatment.
**Artificial saliva was refreshed daily after the acid challenge.

Each day included two 2-minute treatment periods performed an hour apart, followed by one 4-hour carbopol-lactic acid challenge, and finally two additional 2-minute treatment periods. Each treatment was comprised of 5 mL test group plus 10 mL distilled water. Each test group included a negative control (distilled water) and a positive control (fluoride solution). Between the daily treatments and acid challenge, specimens were immersed in artificial saliva.

At the end of each pH cycling study, enamel specimens were examined for surface and longitudinal microhardness. For surface microhardness studies, the change in Vickers hardness number ($\Delta$VHN) was determined as the difference between the post and baseline values ($\Delta$VHN=VHN$_{post}$–VHN$_{base}$), with the post value determined using the same Vickers indenter conditions (200 gf, 15 sec dwell time). Following surface analysis, samples were either examined for fluoride content by extracting enamel biopsies, or they were cross-sectioned and their longitudinal microhardness was measured. Longitudinal microhardness was perforated with the Knoops indenter fitted on the microhardness tester. A series of three indentations per specimen were made under 1) a 10 gf load at 12.5, 25, 37.5, and 50 μm, 2) a 25 gf load at 25, 37.5, and 50 μm, and 3) a 50 gf load used at increments between 25 and 300 μm below the specimen surface, resulting in a total of 57 indents per specimen. The resultant Knoops indentation lengths were then converted to Knoops penetration depths.

Fluoride uptake measurements were performed by taking enamel biopsies, powdering the enamel, and then dissolving the powdered enamel and measuring the fluoride content using a fluoride-sensitive electrode. The measured fluoride was subsequently converted to micrograms of fluoride (μg F) per volume of drilled enamel.

Bioavailable fluoride measurements in the NaF solutions and suspensions are summarized in Table 3.

TABLE 3

Bioavailable fluoride for NaF solutions and suspensions determined using a fluoride-sensitive electrode.

| System | Mean ± SD Bioavailable F—, ppm |
|---|---|
| DI Water | <0.4 |
| 500 ppm F | 505.2 ± 0.0 |
| 500 ppm F + 80 ppm fTCP | 511.0 ± 1.9 |
| 950 ppm F | 946.9 ± 8.3 |
| 950 ppm F + 500 ppm fTCP | 946.9 ± 8.3 |
| 5000 ppm F | 4965.1 ± 11.9 |
| 5000 ppm F + 800 ppm fTCP | 4944.5 ± 11.9 |

The distilled (DI) water had less than 1 ppm of measureable ionic fluoride. Incorporation of 80 ppm fTCP into the NaF (aq) solution produced nearly the same level of bioavailable fluoride relative to the 500 ppm F control; likewise, fTCP produced statistically similar levels of bioavailable fluoride for both 950 and 5000 ppm F.

Figure 6A:
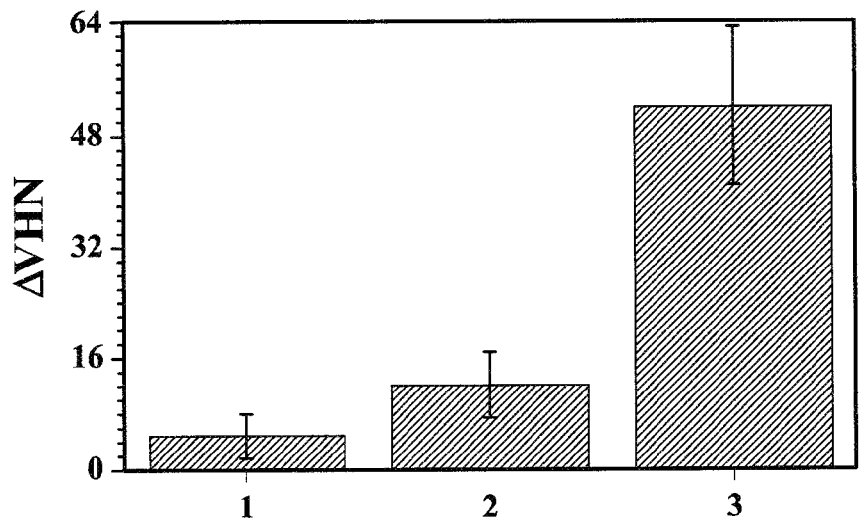
FIG. 6A is a first graph illustrating the effects of fluoride alone and with fTCP on enamel hardness according to one embodiment of the present novel technology.
Figure 6B:
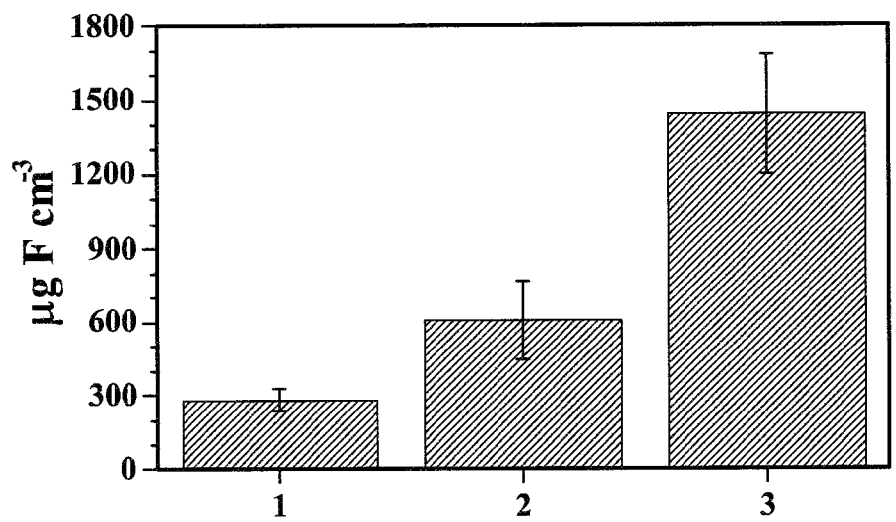
FIG. 6B is a first graph illustrating the fluoride uptake of fluoride alone and with fTCP for enamel according to one embodiment of the present novel technology.

The results from a six-day pH cycling study evaluating 500 ppm F with and without fTCP 60 are shown in FIGS. 6A and 6B. The VHN and fluoride uptake for the specimens treated with 500 ppm F is about 2 times greater than that of specimens treated with DI water. When fTCP 60 is incorporated into the 500 ppm F solution, the VHN is about 4 times greater than for specimens treated only with 500 ppm F, and about 8 times that of the DI reference specimens. The fTCP treated specimens experienced about twice as much fluoride uptake into the enamel relative to the positive control (500 ppm F) samples. The mean (±SEM) penetration depths of the Vickers indenter on the enamel surfaces for the three groups were 12.2±0.7 μm, 11.4±0.5 μm, and 8.8±0.5 μm for DI water, 500 ppm F, and 500 ppm F+100 ppm fTCP, respectively.

Figure 7:
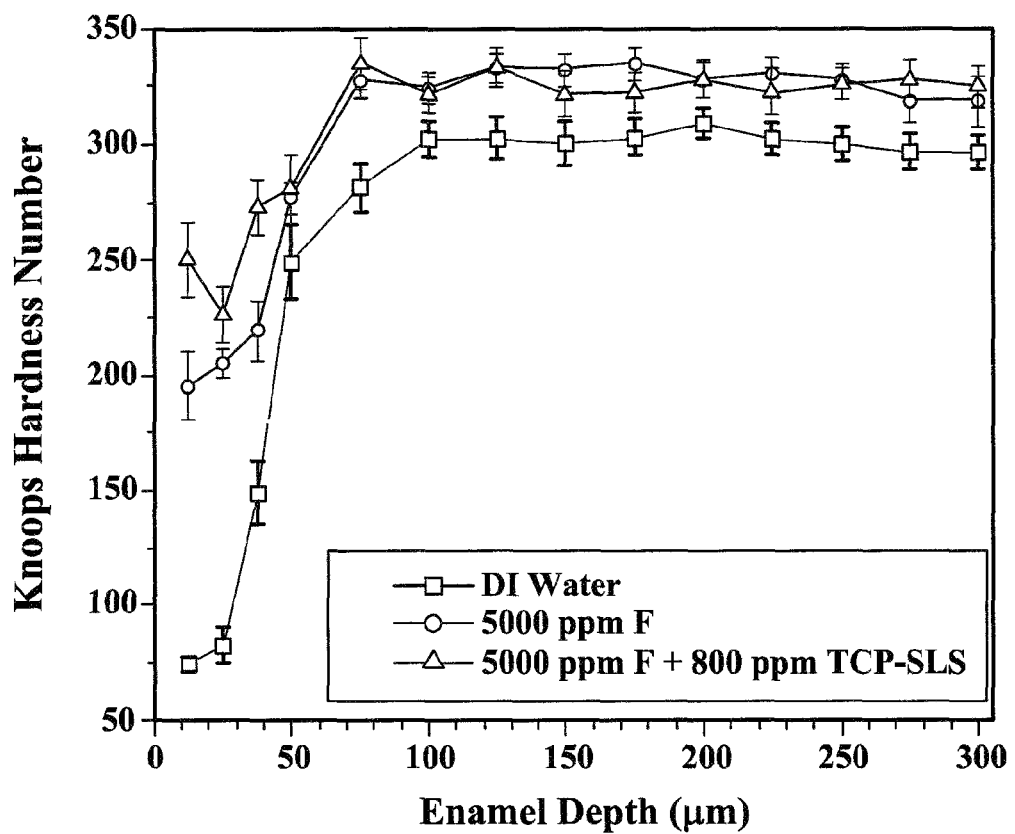
FIG. 7 is a plot of enamel hardness against depth for teeth treated with DI water, 5000 ppm fluoride solution and 5000 ppm fluoride solution with 800 ppm SLS-TCP according to one embodiment of the present novel technology.

FIG. 7 summarizes the results of respective pH cycling studies on the effects of high concentrations of fluoride, with and without fTCP 60, in term of enamel hardness vs. enamel depth. FIG. 7 shows the hardness vs. depth results for a DI water negative control, a 5000 ppm fluoride positive control and a 5000 ppm fluoride plus 900 ppm SLS-TCP test group. Again, the negative control exhibited less hardness over the range of enamel depths observed, with the SLS-TCP containing group exhibiting greater hardness than the 5000 ppm fluoride positive control group up to an enamel depth of about 50 μm. At greater depths, the positive control group and the functionalized TCP containing test group performed about the same. Thus, bioavailable fluoride does not appear to be compromised with the addition of fTCP 60. Since bioavailable calcium and fluoride typically react with one another to produce CaF$_2$ prior to contact with the dentition, this is the first form of bioavailable calcium that is compatible with NaF in both an aqueous and single-compartment format.

In Vitro Enamel Remineralization Using Functionalized TCP and Fluoride

Figure 8:
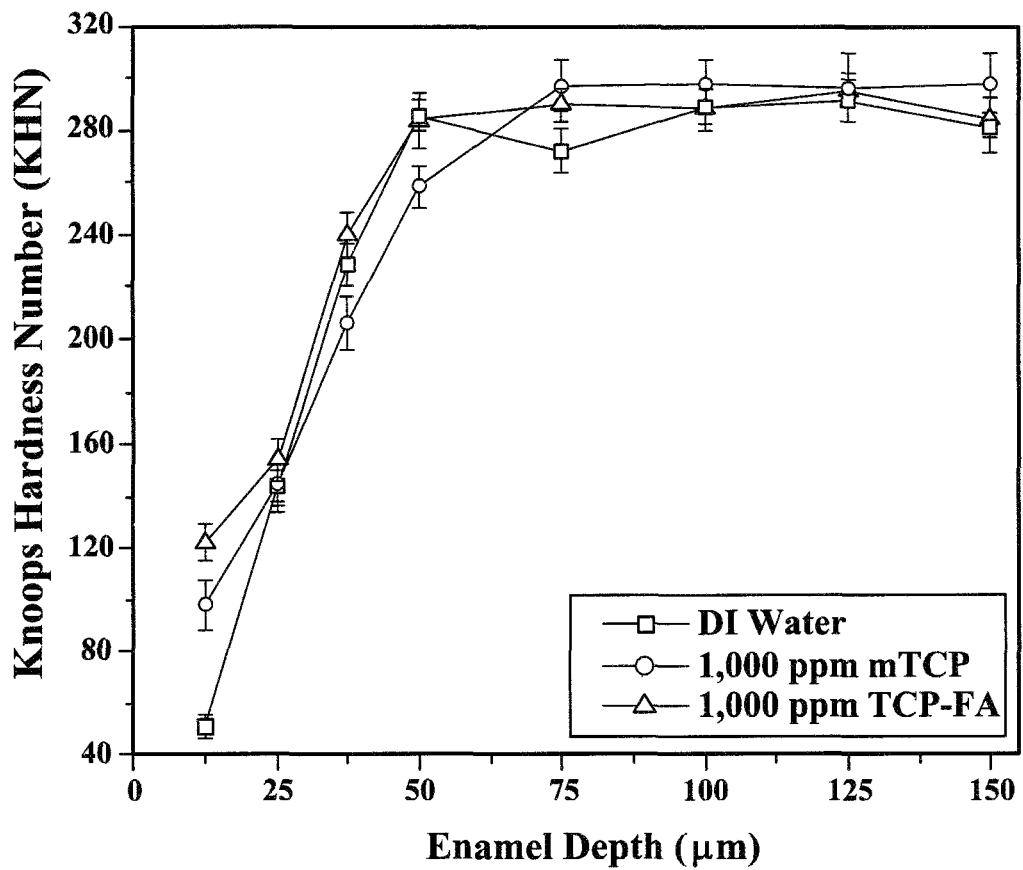
FIG. 8 is a plot of enamel hardness against depth for teeth treated with DI water, 1000 ppm milled TCP solution and 1000 ppm FA-TCP according to one embodiment of the present novel technology.

A study similar to that discussed above regarding fluoride containing compositions was conducted to assess the effects of milling and the resultant lattice distortions on dental remineralization as evidenced by enamel hardening. FIG. 8 summarizes the results of respective pH cycling studies on the efficacy of milled TCP, with and without functionalization with FA, in term of enamel hardness vs. enamel depth. FIG. 8 shows the hardness vs. depth results for a DI water negative control, a 1000 ppm FA-TCP positive control and a 1000 ppm milled TCP test group. The negative control group exhibited less hardness over the shallower range of enamel depths observed, while all three sample groups exhibited similar hardness over the greater enamel depths.

Dental Calcium Delivery Compositions

In one aspect, the present novel technology relates to various comestible compositions, including, for example, candies, confections, chewing gums, lozenges, mints, and the like, as well as to gels, pastes and other additional dentifrices, while in other embodiments, the present novel technology may be applied to coatings for flosses, brush bristles, and the like. In one particular embodiment, the present novel technology includes an organically functionalized calcium phosphate material 60 incorporated into a dental delivery system 70. The dental delivery system 70 is typically water-insoluble and may include a (typically water soluble) flavoring agent. Typically, the organically functionalized calcium phosphate material 60 is dissolved and calcium is released over a predetermined time period while in the oral environment. More typically, the functionalized calcium phosphate material is present in an amount between about 0.001 and about 15 weight percent, depending upon the delivery mechanism and it expected residence time in the oral cavity, the nature of the dental issue being addresses, and the like. Even more typically, surfactant functionalized calcium phosphate material is present in an amount between about 0.001 and about 0.005 weight percent with fluoride concentrations of between about 200 ppm and about 300 ppm. Still more typically, edible acid functionalized calcium phosphate material is present in an amount between about 0.1 and about 5 weight percent in comestible products such as mints, lozenges, and gums. The delivery systems 70 may be aqueous (washes, rinses, and the like) or non-aqueous (varnishes, coating and the like). Fluoride (such as NaF) may be present in concentrations ranging from a few ppm up to 25000 ppm or more.

The amount of functionalized calcium phosphate material 60 is selected such that the dissolution/release of calcium into the oral cavity during residence of the dental delivery system 70 is sufficient to effect remineralization of the teeth. This amount is a function of the composition of the functionalized calcium phosphate material 60 (i.e., the relative amounts of calcium phosphate to surfactant, the type of surfactant selected, and the mineralogical nature of the starting calcium phosphate material). In other words, the organically functionalized calcium phosphate material 60 may be tailored for quicker or slower release, and thus greater bioavailability, of its calcium per unit volume of material. Typically, the organically functionalized calcium phosphate material 60 is functionalized with SLS or the like for slow release (due to its slower dissolution rate) or with FA or the like for quicker calcium release (due to its higher dissolution rate), depending on such factors as expected oral cavity residence time, the nature of the dental remineralization requirements, and the like.

When combined with or including fluoride, the formation of $CaF_2$ is inhibited in the delivery system 70 by the functional organic groups 20 bonded to or wrapping the core inorganic material 10, allowing delivery of both bioavailable calcium and bioavailable fluoride to the target tooth. This is illustrated in FIG. 9

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

What is claimed is:

1. A dental remineralizing delivery system, comprising:
a comestible material; and
a functionalized calcium-containing material including an organic surfactant portion mechanochemically bonded to a distressed calcium phosphate portion and blended with the comestible material;
wherein the organic surfactant portion is between 1 and 30 weight percent of the functionalized calcium-containing material; and
wherein the functionalized calcium-containing material is characterized by a solubility in an oral environment substantially different than that of non-functionalized beta tricalcium phosphate.

2. The dental remineralizing delivery system of claim 1 wherein the organic surfactant is sodium lauryl sulfate.

3. The dental remineralizing delivery system of claim 1 wherein the calcium phosphate portion is beta tricalcium phosphate.

4. The dental remineralizing delivery system of claim 1 wherein the comestible is selected from the group including candies, mints, gums, and lozenges.

5. The dental remineralizing delivery system of claim 2 wherein fluoride is added to the comestible in a concentration of between 100 ppm and 25000 ppm and wherein the functionalized calcium-containing material is added to the comestible in a concentration of between 0.001 and 5 weight percent.

6. The dental remineralizing delivery system of claim 1 and further comprising fluoride added to the comestible in a concentration of between 100 ppm and 25000 ppm.

7. The dental remineralizing delivery system of claim 1 wherein the functionalized calcium-containing material is able to penetrate dentition to a depth of at least 10 microns to effect remineralization thereof.

8. The dental remineralizing delivery system of claim 1 wherein the functionalized calcium-containing material is able to penetrate dentition to a depth of at least 80 microns.

9. The dental remineralizing delivery system of claim 2 wherein the functionalized calcium-containing material is added to the comestible in a concentration of between 0.001 and 15 weight percent.

10. A dental remineralizing composition, comprising in combination:
a distressed calcium phosphate portion;
an organic portion mechanochemically bonded to the distressed calcium phosphate portion to define a functionalized calcium phosphate portion; and
an edible delivery portion blended with the functionalized calcium phosphate portion;
wherein the organic portion is between 1 and 30 weight percent of the functionalized calcium phosphate portion; and
wherein the functionalized calcium phosphate portion is differently soluble in an oral environment than is non-functionalized beta tricalcium phosphate.

11. The dental remineralizing composition of claim 10 wherein the organic portion is a surfactant.

12. The dental remineralizing composition of claim 11 wherein the surfactant is sodium lauryl sulfate.

13. The dental remineralizing composition of claim 10 wherein the edible delivery portion is selected from the group including candies, mints, gums, and lozenges.

14. The dental remineralizing composition of claim 10 wherein fluoride is added to the edible delivery portion in a concentration of between about 100 ppm and 25000 ppm and wherein the functionalized calcium phosphate portion is added to the comestible in a concentration of between 0.001 and 5 weight percent.

15. The dental remineralizing composition of claim 10 and further comprising fluoride added to the edible delivery portion in a concentration of between 100 ppm and 25000 ppm.

16. The dental remineralizing composition of claim 10 wherein the functionalized calcium phosphate portion is able to penetrate dentition to a depth of at least 10 microns to effect remineralization thereof.

17. The dental remineralizing composition of claim 10 wherein the functionalized calcium phosphate portion is able to penetrate dentition to a depth of at least 80 microns.

18. The dental remineralizing composition of claim 10 wherein the functionalized calcium phosphate portion is added to the edible delivery portion in a concentration of between 0.001 and 15 weight percent.

19. A dental remineralizing composition, comprising in combination:
- a distressed tricalcium phosphate portion wherein at least a portion of the tricalcium phosphate lattice has been physically distorted;
- an organic surfactant portion mechanochemically bonded to the distressed tricalcium phosphate portion to define a functionalized tricalcium phosphate portion; and
- an edible portion mixed with the functionalized tricalcium phosphate portion;
- wherein the organic surfactant portion is between 1 and 30 weight percent of the functionalized tricalcium phosphate portion;
- wherein the functionalized tricalcium phosphate portion is more soluble in an oral environment than is non-functionalized beta tricalcium phosphate;
- wherein the functionalized calcium phosphate portion is able to penetrate dentition to a depth of at least 80 microns; and
- wherein the functionalized calcium phosphate portion is added to the edible delivery portion in a concentration of between 0.001 and 15 weight percent.

* * * * *